United States Patent [19]

Allor

[11] Patent Number: 4,478,223
[45] Date of Patent: Oct. 23, 1984

[54] THREE DIMENSIONAL ELECTROCARDIOGRAPH

[76] Inventor: Douglas R. Allor, 17190 E. Warren Ave., Detroit, Mich. 48224

[21] Appl. No.: 447,155

[22] Filed: Dec. 6, 1982

[51] Int. Cl.³ .......................................... G06K 15/20
[52] U.S. Cl. .................................... 128/699; 128/731
[58] Field of Search ............................... 128/695-696, 128/699, 710, 712, 731, 733

[56] References Cited

U.S. PATENT DOCUMENTS

| | | | |
|---|---|---|---|
| 3,548,813 | 12/1970 | Berner | 128/699 |
| 3,841,309 | 10/1974 | Salter et al. | 128/731 |
| 3,983,867 | 10/1976 | Case | 128/710 |
| 4,323,079 | 4/1982 | Demetrescu | 128/731 |
| 4,328,491 | 5/1982 | Demetrescu | 128/731 |

OTHER PUBLICATIONS

Chatterjee et al., "A VCG System with Temporal Dimension, Directional Reference and Display of Component Loops", J. Biomed. Eng., (1982), vol. 4, No. 2, (Apr.), pp. 149-152.

Tönnies Medical Electronics, "The New Tönnies Stereokinematic Vector Cardiograph", Technical Bulletin, Aug. 1979.

Vrohet et al., "The Computer System for Analysis Display and Storage of Vector Cardiograms", Proc. Comp. in Cardiology, Rotterdam, Netherlands, Sep. 29-Oct. 1, 1977, pp. 785-789.

Silcocks et al., "Various Methods of Displaying Computer Generated Three Dimensional Electrocardiograms", Proc. 7th Annual Biomed. Sci. Inst. Symposium on Imagery in Medicine, Ann Arbor, Mich., USA, May 19, 1969, pp. 37-43.

Primary Examiner—William E. Kamm
Assistant Examiner—Mitchell J. Shein
Attorney, Agent, or Firm—Fisher, Crampton, Groh & McGuire

[57] ABSTRACT

This invention relates to a system for the clinical measurement of the electrical potential of a biological system using non-invasive monitoring equipment.

5 Claims, 2 Drawing Figures

THREE DIMENSIONAL ELECTROCARDIOGRAPH

In one aspect this invention relates to clinical analysis of a living biological system having characteristic electrical potential. In a further aspect this invention relates to non-invasive monitoring, recording and display in real time of the actions of a biological system with a characteristic electro-physichogial potential available for non-invasive measurement and display.

Initially measuring the electrical signals generated by a biological system such as a heart His Bundle and Purkinje fiber network involved the placing of an electrical catheter in the right ventricle of the heart. Such invasive techniques have a traumatic affect upon the patient with possible attendant complications. A non-evasive form of cardiography was subsequently developed. One form of non-invasive His Bundle cardiography was described in Wajszczuk et al, "Non-invasive recording of His Purkinje Activity in Man by QRS-Triggered Signal Averaging", *Circulation*, July, 1978. This technique measured a number of signals emanating from the heart in an analog format and converted the signals to digital format. After conversion to a digital format the signals were averaged over a large number of consecutive heartbeats, such as, 128 to 256 heartbeats to provide an acceptable signal-to-noise ratio. This technique gives only averages and does not disclose irregular beat patterns which may be occurring within the sample size.

Also, such systems do not provide a three-dimensional analysis of the biological system.

In an attempt to improve on the analysis provided by the standard two-dimensional cardiology charts various techniques have been proposed to provide a three-dimensional vector cardiogram. One example of a three-dimensional vector cardiogram is disclosed in "The Frame of Reference of Three-Dimensional Vector Cardiograms Drawn by a Computer Cathode Ray Tube", *Cardiovascular Research*, Vol. 3, (1969) 227–234. This article details a method of using a computer to generate solid looking figures on a cathode ray tube traced by a point generator and represents two-dimensional topological curves. Such a device does not provide a clear three-dimensional picture of the biological system being studied but rather presents only a simple line drawing of a computerized vector.

A second system is described in Shander, "A New Three-Dimensional Display of the Vector Cardiogram Employing Holigraphy", *Chest*, Vol. 59, #4, April, 1971, 438–440. Shander describes a method for taking cardiogram vector traces from an osilloscope screen employing the use of an optical laser system to provide a holographic plate from the three separate vector cardiogram loops which again only presents a simple line drawing of a basic computerized vector display.

None of the references cited above discloses a method for forming a three dimensional representation in any form of the electrical pattern of a biological system, such as the heart or brain. The above references while providing improved diagnostic tools generally use a number of measurements and calculate an average. Thus, any arrhythmias or other unusual electrical activity which occur will be disguised by virtue of the averaging process.

It is an object of this invention to provide a three-dimensional diagram of the electrical conduction pathways of a biological system.

It is a further object of this invention to provide a three-dimensional diagram in real time showing the variations in electrical conduction pathways from moment to moment in the biological system.

Briefly, the system of this invention provides a real time, three dimensional analysis of the electrical activity of a patient's organ, such as a heart, without the use of invasive measures. The system comprises first, second and third pairs of non-invasive electrodes attached to the body. First, second and third associated pre-amplifications means are attached to the electrodes to process the electrical signals generated by the organ being studied to develop electrical signals characteristic of the plane through the organ represented by the corresponding set of electrodes. An analyzer takes the three signals and analyzes the signals by virtue of the phase differences to provide a three dimensional real time diagram of the electrical activity of the organ being studied.

In the accompanying drawing in which like numerals refer to like parts:

In general, various organs in the human body such as the brain and heart have major conduction pathways and electrical activity during function. As the organ functions, electrical currents move back and forth through the living tissue. By means of this invention, the conduction pathways can be located and shown in a three dimensional representation. A three dimensional real time representation provides a method for generating and analyzing invaluable diagnostic information about the organ's functioning. For example, in cardiology, the technique could be used to give information about infarct size after a heart attack. A three dimensional representation of the electrical conductivity of the surface of the heart would show an infarct displayed as a hole or lack of electrical activity due to the dead myo-cardium tissue lacking electrical conductivity. The three dimensional representation can also be used in drug studies to show changes in the cardiac conduction pattern caused by the drug after administration, both as a function of time and dose. Since the system functions in real time and does not use averages, it can analyze even short lived effects which function for a few beats whereas previous systems which used averages for a large number of beats would not detect short term effects. As shown, the measurement of the heart would normally be used to display one complex since there is a delay in conductive activity between the upper and lower heart chambers.

Figure 1:
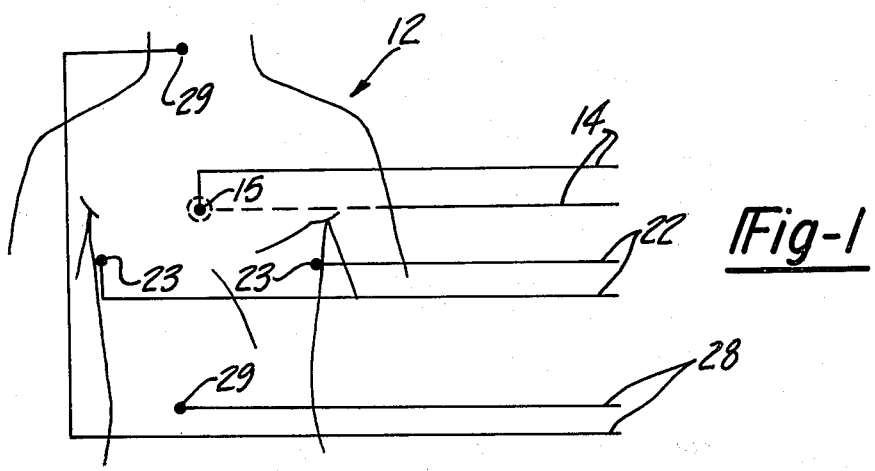
FIG. 1 is a block diagram of a system of one embodiment of the invention.
Figure 2:
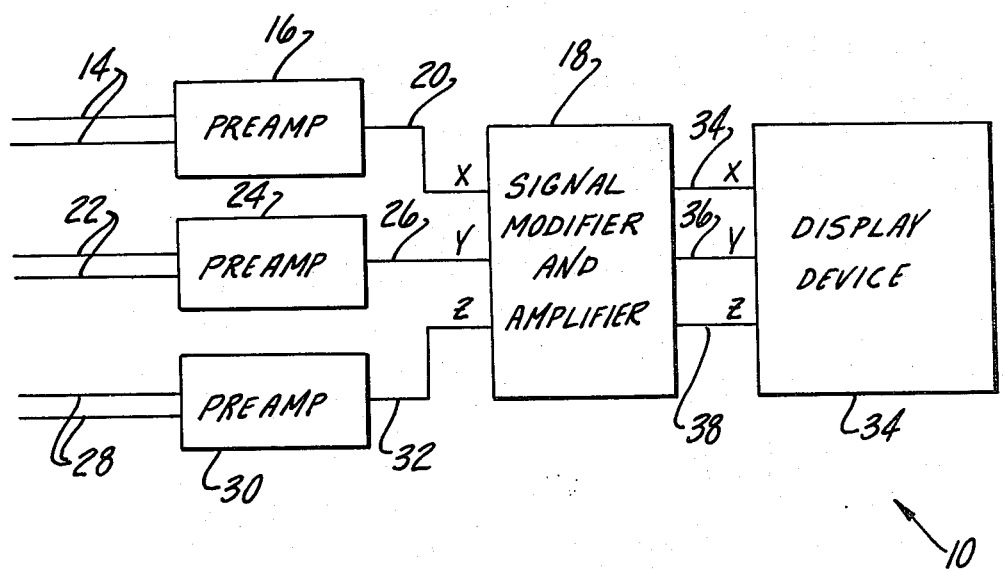
FIG. 2 is a chest diagram showing possible locations for electrode placement in accordance with one aspect of invention.

Referring to FIGS. 1 and 2, a system 10 assembled in accordance with this invention is connected to the body of a patient 12 to monitor the patient's heart. A first set of leads 14 connect the electrodes 15 on the body 12 to a first preamplifier 16. The preamplifier 16 generates a first amplified output signal characteristic of the plane through the heart being represented by the first set of electrodes. The first modified output signal is fed to a signal modifier and amplifier 18 by means of a lead 20.

A second set of leads 22 connect the electrodes 23 on the body 12 to a second preamplifier 24 to provide a second signal which provides a second modified amplified signal to the amplifier 18 by lead 26.

A third set of leads 28 connect the electrodes 29 to a third preamplifier 30 which provides a third amplified signal to the signal modifier and amplifier 18.

One example of an acceptable preamplification system useful in the practice of this invention is described more fully in U.S. Pat. No. 4,261,369 issued to Douglas R. Allor. The main components of such a preamplifier include a differential amplifier, switch selectable high pass filter, switch selectable low pass filter and a variable gain amplifier.

The low pass and high pass filter are separately adjustable so as to allow adjustment by the equipment operator in accordance with ambient conditions. It may be necessary to adjust the filters in response to patient muscle noise and/or extraneous electro-magnetic interference.

Where the preamplifier is being used to monitor the electrical cardiac activity the system frequency response will generally be maintained in the range of 30 to 1000 Hz and for monitoring the brain the frequency will generally be about 5 to 1000 Hz. The filters can be adjusted so as to monitor the frequencies characteristic of the organ being analyzed. The separate high pass and low pass filter allow the system to be adjusted so as to empirically match the overall characteristics of the system. The preamplifiers 16, 24, and 30 will condition the incoming analog signal and provide a modulated or modified output signal which is characteristic of the plane in which the electrodes lie.

The three modified signals from the preamplifier are fed via the connecting leads to the signal modifier and amplifier 18.

The amplifier 18 will amplify the three modified signals and transmit the signals as amplified analog signal via lead 34, 36, and 38 to a display and/or analysis device. One example of a suitable signal modifier useful in the practice of this invention would be the Oei model 66700 available from Optical Electronics, Inc. The amplified signals generated by the Oei amplifier are suitable for display on a cathode ray tube, or other analysis device. If desired, the amplified signal can be fed into an analog-to-digital converter and the resulting digital signals stored in digital form for computer analysis.

One example of a suitable display device which can receive the amplified signals is a Phillips Dual Trace Scope such as that commonly available under the model no. 3217. The scope will analyze the phase differences in the three amplified signals and produce a three dimensional representation of the electrical conductive pathways of the organ being analyzed. In addition to or instead of displaying the representation on a CRT, the signals can be fed to a paper tracing or plotter which generates a three dimensional representation of the electrical activity occurring in the organ being analyzed.

In addition to or instead of the analog signals from the amplifier can be fed directly to a computer for conversion into digital format and the data stored on a magnetic storage medium for later or further analysis. The digital representation of the various heartbeats can be analyzed by means of computer programs to ascertain whether or not there are substantial variations in the characteristics of the electrical conductivity at various defined portions of the heartbeat. For example, in cardiology where individual heartbeats are analyzed, the computer could be programmed to select those heartbeats which are markedly different from the normal for the patient, or in the case of average values are significantly different in one or more aspects from the average values. The heartbeats could be analyzed to isolate and display various arrhythmias so as to aid diagnosis by isolating problem areas.

The foregoing discussion has been related primarily to cardiology testing, research and measurement. However, this invention can also be used to measure the electrical activity from the brain of a patient in a similar manner with the electrodes being placed on the head so as to measure the conductive potential of the electrical currents moving through the brain. In this respect, it is useful for studying the effects of strokes, on various portions of the brain, and also the changes brought about in the electrical conductive potential of the brain by actions of various drugs.

Because the system of this invention operates in the real time mode it will show the major conduction pathways of the heart or other organs for inspection. The pathways will be represented in their proper spatial location and the conduction times and activity will be clearly visible. Being able to observe the current flow through the organ will allow a more detailed analysis and diagnosis of the organ being studied. The effects of drugs or physically induced abnormalities on the electrical conduction activity of the organ will also be clearly shown. In addition to a three dimensional representation, the conduction times along the conduction pathways can be observed as the conduction takes place.

Various modifications and alternation of this invention will become obvious to those skilled in the art without departing from the scope and spirit of this invention and it is understood that this invention is not limited to the illustrative embodiment set forth hereinbefore.

What is claimed is:

1. Means for the non-invasive real time three-dimensional analysis of the electrical activity of a patient's organ comprising:
    a first set of paired electrodes, a first preamplification means for developing a first modulated electrical signal characteristic of the plane through the organ represented by said first electrodes based on the electrical signals received from said first electrodes;
    a second set of paired electrodes, a second preamplification means for developing a second modulated electrical signal characteristic of the plane through the organ represented by said second electrodes based on the electrical signals received from said second electrodes;
    a third set of paired electrodes, a third preamplification means for developing a third modulated electrical signal characteristic of the plane through the organ represented by said third electrodes based on the electrical signals received from said third electrodes;
    signal means for modifying and amplifying said first, second, and third modulated electrical signals; and
    means for receiving said first, second, and third amplified modulated signals and analyzing said signals in a three-dimensional coordinate system based on the phase differences between said signals.

2. The system of claim 1 further including means for plotting a three-dimensional representation of the conductive potential of the organ on a permanent substrate material.

3. The system of claim 1 wherein said analysis means is a cathode ray tube.

4. The system of claim 1 wherein said preamplification means includes bandpass filter means for minimizing extraneous electrical interference.

5. The system of claim 4 wherein said bandpass filter means operates in the range of 5 to 1000 Hz.

* * * * *